(12) United States Patent
Davis

(10) Patent No.: US 11,033,421 B1
(45) Date of Patent: Jun. 15, 2021

(54) DEVICE TO PREVENT SNORING

(71) Applicant: Paul M. Davis, Broken Arrow, OK (US)

(72) Inventor: Richard B. Davis, Sand Springs, OK (US)

(*) Notice: Subject to any disclaimer, the term of this patent is extended or adjusted under 35 U.S.C. 154(b) by 480 days.

(21) Appl. No.: 14/829,699

(22) Filed: Aug. 19, 2015

Related U.S. Application Data

(60) Provisional application No. 62/070,499, filed on Aug. 27, 2014.

(51) Int. Cl.
*A61F 5/00* (2006.01)
*A61F 5/56* (2006.01)

(52) U.S. Cl.
CPC .................. *A61F 5/566* (2013.01)

(58) Field of Classification Search
CPC ... A61F 5/56; A61F 5/566; A61C 5/14; A61C 7/08; A61C 7/36; A63B 71/085
USPC .... 433/5–8, 19, 24, 140; 128/848, 859, 861, 128/862
See application file for complete search history.

(56) References Cited

U.S. PATENT DOCUMENTS

| | | | | |
|---|---|---|---|---|
| 3,132,647 A * | 5/1964 | Corniello | ............... | A61F 5/566 128/848 |
| 4,955,393 A * | 9/1990 | Adell | .................. | A63B 71/085 128/859 |
| 6,976,491 B2 * | 12/2005 | D'Agosto | ............... | A61F 5/566 128/200.24 |
| 8,474,462 B2 * | 7/2013 | Makower | ............... | A61F 5/566 128/860 |
| 8,656,921 B2 * | 2/2014 | Zhang | ..................... | A61F 5/566 128/848 |
| 8,833,374 B2 * | 9/2014 | Fallon | ..................... | A61F 5/566 128/848 |
| 2013/0125902 A1 * | 5/2013 | Danielian | .............. | A61B 17/24 128/859 |

* cited by examiner

*Primary Examiner* — Rachael E Bredefeld
*Assistant Examiner* — Adam Baker
(74) *Attorney, Agent, or Firm* — Margaret S. Millikin

(57) ABSTRACT

The present invention is a two part device to prevent a person from snoring consisting of a mouth guard with an attached tongue suppressor. The tongue suppressor attaches to the mouth guard in a manner so that it is adjustable in length and creates a downward pressure on the base of the tongue. The underside of the tongue suppressor has ridges that angle forward to engage papillae on the tongue and thereby prevent the tongue from moving rearward in the mouth during sleep.

13 Claims, 2 Drawing Sheets

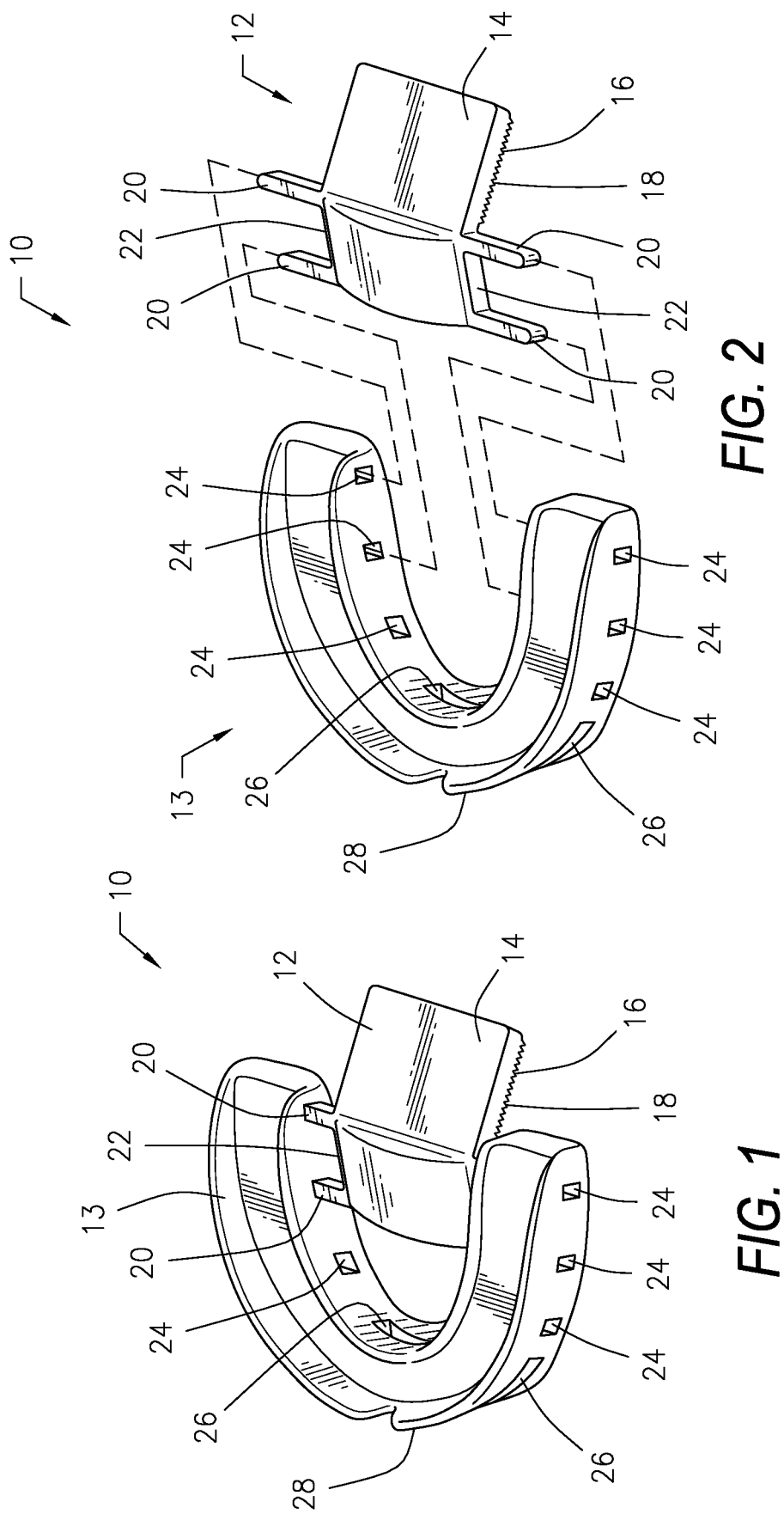

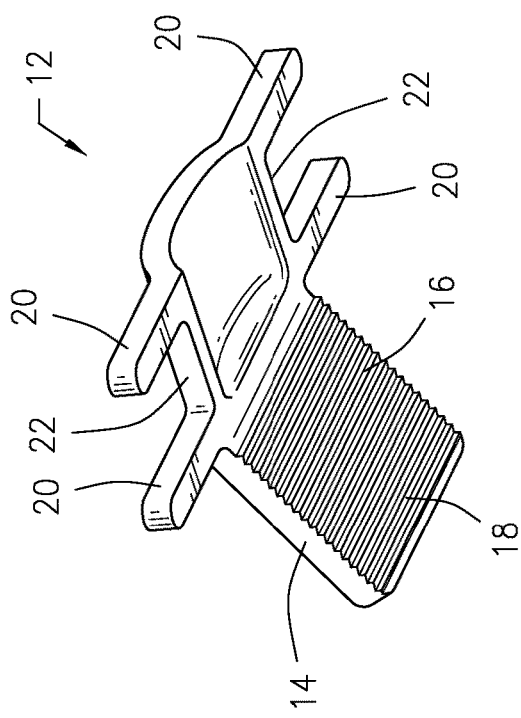
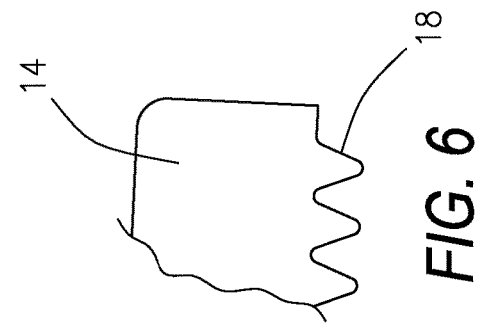
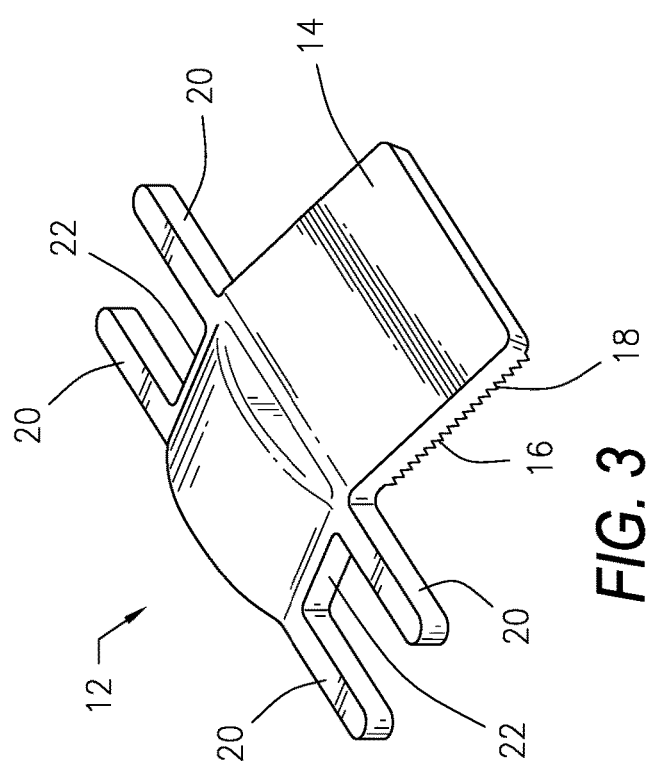
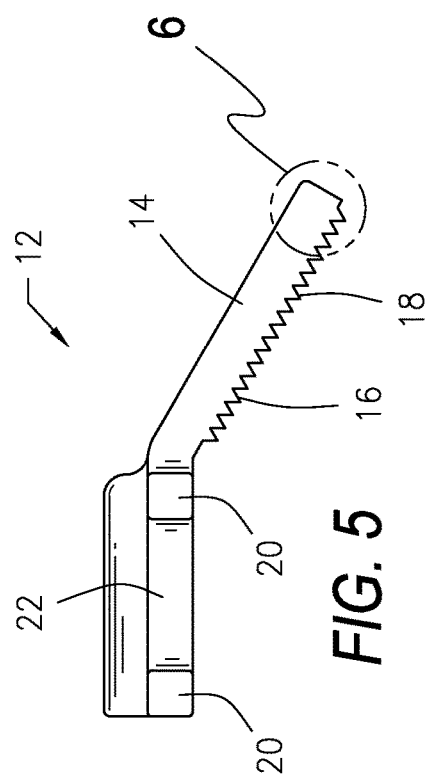

DEVICE TO PREVENT SNORING

CROSS-REFERENCE TO RELATED APPLICATIONS

The present application claims priority to U.S. Provisional Patent Application Ser. No. 62/070,499 filed on Aug. 27, 2014 for the invention entitled Sound Slee . . . p Mouthguard.

BACKGROUND OF THE INVENTION

1. Field of the Invention

The present invention is a device to prevent a person from snoring. Specifically it is a mouth guard with an attached tongue suppressor. The tongue suppressor attaches to the mouth guard in a manner so that it is adjustable in length and creates a downward pressure on the base of the tongue. The underside of the tongue suppressor is provided with micro ridges that are angled forward to engage papillae on the tongue and thereby prevent the tongue from moving rearward in the mouth during sleep.

2. Description of the Related Art

Sleep apnea typically is caused when the tongue moves rearward in the mouth when a person is asleep, thereby causing snoring and temporary secession of breathing as the tongue blocks the person's airway. For a person with severe sleep apnea, breathing may be interrupted frequently and for long durations, causing the person to be awakened multiple times during a given period of sleep and resulting in sleep deprivation.

Various devices have been used to prevent snoring and sleep apnea. One such device is a continuous positive air pressure or CPAP machine. A CPAP machine is an air pump that provides air to a patient's nose via an air line and the pressurized air prevents the throat from closing during sleep, thereby preventing snoring and sleep apnea. Testing for sleep apnea and purchasing a CPAP machine are somewhat expensive and thus many people do not find this to be a viable option for them.

Another device to prevent snoring and sleep apnea is a mouth piece that forces the lower jaw forward so that the tongue cannot fully close off the patient's airway. This type of device is much less expensive than a CPAP machine and thus is affordable for most people. However, one of the problems with this type of device is that it holds the jaw in an unnatural and uncomfortable position which can cause damage to the jaw.

In addition to the various devices that have been used to treat snoring and sleep apnea, surgical remedies are available. These surgical procedures include tonsillectomy, uvulectomy, adenoidectomy, and inserting of metal rods at the base of the tongue to create scar tissue which can help to prevent the tongue from sliding backward during sleep. Each of these procedures is painful, expensive, potentially dangerous, and may not be effective in eliminating the person's snoring and sleep apnea. The inventor has had each of these surgical procedures performed on him without success in solving his snoring problem.

The present invention addresses the problem in a different manner by providing a tongue suppressor that is held in the mouth by a mouth guard. The tongue suppressor exerts a gentle downward pressure on the base of the tongue and a lower side of the tongue suppressor is equipped with forwardly extending micro ridges that engage the papillae of the tongue to hold the tongue in position within the mouth and prevent the tongue from falling rearward. This prevents the tongue from blocking the person's airway when they are sleeping.

The device is adjustable in length and in width to fit any size of mouth. This device is comfortable to wear as it holds the jaw and tongue in their natural and comfortable position. The device includes air openings so that even mouth breathers can use it without obstructing their normal breathing pattern.

SUMMARY OF THE INVENTION

The present invention is a two piece device for preventing snoring and sleep apnea. The invention includes a mouth guard that is designed to fit over a person's upper teeth and a tongue suppressor that adjustably attaches to the mouth guard. The tongue suppressor is held in position within the mouth by the mouth guard.

The rear of the tongue suppressor is downwardly angled so as to exert gentle pressure on the base of the person's tongue. The tongue suppressor is preferably semi-flexible to make it more comfortable and to help it maintain contact with the tongue even for those people who tend to partially open their mouth when breathing, i.e. mouth breathers. The mouth guard may be slightly deeper than most mouth guards so that it still functions well for mouth breathers.

A lower side of the tongue suppressor is equipped with forwardly extending micro ridges that engage the papillae of the tongue to hold the tongue in position within the mouth and prevent the tongue from falling rearward. The combination of the downward pressure exerted on the tongue by the tongue suppressor and the micro ridges that grip onto the tongue's papillae together serve to prevent the tongue from moving rearward and blocking the person's airway when they are sleeping.

The tongue suppressor attaches to the mouth guard with tabs that are provided on the sides of the tongue suppressor and that insert into slots provided in the mouth guard. The device is adjustable in length by the selection of the slots into which the tabs are inserted. The mouth guard is semi-flexible in width to fit any size of mouth.

Because of the adjustability of the device and the semi-flexible nature of the mouth guard and the tongue suppressor, the device is comfortable to wear and allows the jaw and tongue to remain in their natural and comfortable position. The device includes air openings in the front of the mouth guard to allow mouth breathers to use it without obstructing their normal breathing pattern.

BRIEF DESCRIPTION OF THE DRAWINGS

FIG. 1 is a perspective view of a device to prevent snoring that is constructed in accordance with a preferred embodiment of the present invention.

FIG. 2 is an exploded view of the device of FIG. 1, showing the two components.

FIG. 3 is a top isometric view of the tongue suppressor of FIG. 2.

FIG. 4 is a bottom isometric view of the tongue suppressor of FIG. 3.

FIG. 5 is a side view of the tongue suppressor of FIG. 2.

FIG. 6 is an enlarged view of the micro ridges shown within circle A of FIG. 5.

DETAILED DESCRIPTION OF THE PREFERRED EMBODIMENT

Referring now to the drawings and initially to FIGS. 1 and 2, there is illustrated a two piece device 10 for preventing snoring and sleep apnea that is constructed in accordance with a preferred embodiment of the present invention. The device 10 is designed to hold a person's tongue in place while sleeping, thereby keeping the airway open and preventing or dampening the vibrations which cause snoring.

Referring also to FIGS. 3-6, this is accomplished by employing a tongue suppressor 12 that lays down the length of the person's tongue. The tongue suppressor 12 is held in position in the mouth by a mouth guard 13. The mouth guard 13 is designed to fit over a person's upper teeth.

The tongue suppressor 12 contains a slightly downward angled distal portion 14, i.e. the rearwarding extending portion of the tongue suppressor 12. A bottom surface 16 of the distal portion 14 contains micro ridges 18. The downward angled distal portion 14 gently pushes down on the tongue and allows the micro ridges 18 to engage and catch the papillae (follicles) on the tongue. This keeps the tongue in place in the mouth and away from the back of the throat and away from the nasal opening into the nasopharynx. The device 10 does not manipulate the lower jaw to accomplish this, therefore allowing a natural closing of the mouth.

The tongue suppressor 12 is adjustable on the mouth guard 13 both front-to-back and from side-to-side to accommodate various jaw and mouth sizes as will be explained in more detail hereafter.

The downwardly angled distal portion 14 of the tongue suppressor 12 exerts gentle pressure on the base of the person's tongue. The tongue suppressor 12 is preferably semi-flexible to make it more comfortable and to help it maintain contact with the tongue even for those people who tend to partially open their mouth when breathing, i.e. mouth breathers. The mouth guard 13 may be slightly deeper than most mouth guards so that it still functions well for mouth breathers.

As best shown in FIGS. 5 and 6, the micro ridges 18 extend forward to engage the papillae of the tongue to hold the tongue in position within the mouth and prevent the tongue from falling rearward. The combination of the downward pressure exerted on the tongue by the tongue suppressor 12 and the micro ridges 18 that grip onto the tongue's papillae serve to prevent the tongue from moving rearward and blocking the person's airway when they are sleeping.

As shown in FIGS. 1 and 2, the tongue suppressor 12 attaches to the mouth guard 13 with tabs 20 that are provided on the sides 22 of the tongue suppressor 12 and that insert into slots 24 provided in the mouth guard. This tab and slot arrangement allows the tongue suppressor 12 to be slid from side-to-side on the mouth guard 13 to adjust the position of the tongue suppressor 12 relative to the sides 22 of the tongue suppressor 12. The device 10 is also adjustable in length or from front-to-back by the selection of the slots 24 into which the tabs 20 are inserted. The mouth guard 13 is semi-flexible and can be adjusted to fit any size of mouth.

Because of the adjustability of the device 10 and the semi-flexible nature of the mouth guard 13 and the tongue suppressor 12, the device 10 is comfortable to wear and allows the jaw and tongue to remain in their natural and comfortable position. The device 10 includes air openings 26 in the front 28 of the mouth guard 13 to allow mouth breathers to use it without obstructing their normal breathing pattern.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A device to prevent snoring while maintaining in a natural position the lower jaw of a person wearing the device, the device comprising:
    a mouth guard for receiving therein the upper teeth of the person wearing the device;
    a tongue suppressor comprised of a semi-flexible material and attachable to the mouth guard, said tongue suppressor having a distal portion extending rearward from the mouth guard, said distal portion extending downward at an angle from the mouth guard so that the tongue suppressor, when assembled for in-use configuration, exerts a downward pressure against a base of a tongue of the person wearing the device; and
    ridges provided on a bottom surface of the distal portion for engaging papillae on the base of the tongue of the person wearing the device, wherein the device maintains the lower jaw of the person wearing the device in a natural position without forcing forward the lower jaw;
    wherein said ridges are formed on an underside of the downwardly extending distal portion of the tongue suppressor and wherein said ridges are formed to extend generally perpendicularly with respect to the underside of the distal portion of the tongue suppressor so that said ridges extend in a forward direction to engage with papillae on the tongue of the person and prevent the tongue from sliding rearward during sleep;
    wherein, when the tongue suppressor is assembled for in-use configuration, the distal portion of the tongue suppressor moves with the tongue, thereby enabling the person wearing the device to swallow and, after swallowing, due to the forward direction of the ridges on the underside of the distal portion of the tongue suppressor, enabling the tongue to return to rest in a natural position and engaging the papillae of the tongue.

2. A device to prevent snoring according to claim 1 wherein the tongue suppressor forms opposing sides and a plurality of pairs of substantially parallel tabs are provided on the opposing sides of the tongue suppressor;
    wherein the mouth guard forms a plurality of pairs of substantially parallel slots corresponding to the plurality of pairs of substantially parallel tabs; and
    wherein the plurality of pairs of substantially parallel tabs are selectively inserted into the corresponding plurality of pairs of substantially parallel slots to adjustably secure the tongue suppressor to the mouth guard.

3. The device of claim 2 wherein the device is removably adjustable to accommodate various jaw and mouth sizes by selectively inserting the plurality of pairs of substantially parallel tabs into the corresponding plurality of pairs of substantially parallel slots.

4. The device of claim 3 wherein the tongue suppressor extends the length of the tongue.

5. A device to prevent snoring according to claim 1 wherein said ridges are micro ridges.

6. A device to prevent snoring according to claim 1 further comprising:

a front of said mouth guard provided with air openings extending therethough to allow a person to breathe through their mouth when the mouth guard is located in their mouth.

7. A device to prevent snoring while maintaining in a natural position the lower jaw of a person wearing the device, the device consisting essentially of:
 a mouth guard comprised of a semi-flexible material for receiving therein the upper teeth of the person wearing the device;
 a tongue suppressor attachable to the mouth guard, said tongue suppressor having a distal portion extending rearward from the mouth guard, said distal portion extending downward at an angle from the mouth guard so that the tongue suppressor, when assembled for in-use configuration, exerts a downward pressure against a tongue of the person wearing the device; and
 ridges provided on a bottom surface of the distal portion for engaging papillae on the tongue of the person wearing the device, wherein the device maintains the lower jaw of the person wearing the device in a natural position without forcing forward the lower jaw;
 wherein said ridges are formed on an underside of the downwardly extending distal portion of the tongue suppressor and wherein said ridges are formed to extend generally perpendicularly with respect to the underside of the distal portion of the tongue suppressor so that said ridges extend in a forward direction to engage with papillae on the tongue of the person and prevent the tongue from sliding rearward during sleep; and
 wherein, when the tongue suppressor is assembled for in-use configuration, the distal portion of the tongue suppressor moves with the tongue, thereby enabling the person wearing the device to swallow and, after swallowing, due to the forward direction of the ridges on the underside of the distal portion of the tongue suppressor, enabling the tongue to return to rest in a natural position and engaging the papillae of the tongue.

8. A device to prevent snoring according to claim 7 wherein the tongue suppressor forms opposing sides and a plurality of pairs of substantially parallel tabs are provided on the opposing sides of the tongue suppressor;
 wherein the mouth guard forms a plurality of pairs of substantially parallel slots corresponding to the plurality of pairs of substantially parallel tabs; and
 wherein the plurality of pairs of substantially parallel tabs are selectively inserted into the corresponding plurality of pairs of substantially parallel slots to adjustably secure the tongue suppressor to the mouth guard.

9. The device of claim 8 wherein the device is removably adjustable to accommodate various jaw and mouth sizes by selectively inserting the plurality of pairs of substantially parallel tabs into the corresponding plurality of pairs of substantially parallel slots.

10. The device of claim 9 wherein the tongue suppressor extends the length of the tongue.

11. A device to prevent snoring according to claim 7 wherein said ridges are micro ridges.

12. A device to prevent snoring according to claim 7 further consisting essentially of:
 a front of said mouth guard provided with air openings extending therethough to allow a person to breathe through their mouth when the mouth guard is located in their mouth.

13. A method of preventing snoring while maintaining the jaw of a person in a natural position, the method comprising the steps of:
 providing a device comprising a mouth guard comprised of a semi-flexible material for receiving therein the upper teeth of the person wearing the device, a tongue suppressor attachable to the mouth guard, said tongue suppressor having a distal portion extending rearward from the mouth guard, said distal portion extending downward at an angle from the mouth guard so that the tongue suppressor, when assembled for in-use configuration, exerts a downward pressure against a tongue of the person wearing the device;
 providing ridges for engaging the papillae of the tongue thereby preventing the tongue from falling rearward, the ridges provided on a bottom surface of the distal portion for engaging papillae on the tongue of the person wearing the device, wherein the device maintains the lower jaw of the person wearing the device in a natural position without forcing forward the lower jaw and wherein said ridges are formed on an underside of the downwardly extending distal portion of the tongue suppressor and wherein said ridges are formed to extend generally perpendicularly with respect to the underside of the distal portion of the tongue suppressor so that said ridges extend in a forward direction to engage with papillae on the tongue of the person and prevent the tongue from sliding rearward during sleep and, after swallowing, enabling the tongue to return to rest in a natural position and engaging the papillae of the tongue; and exerting a downward pressure against the base of a tongue of a person wherein, when the tongue suppressor is assembled for in-use configuration, the distal portion of the tongue suppressor moves with the tongue, thereby enabling the person wearing the device to swallow and, after swallowing, due to the forward direction of the ridges on the underside of the distal portion of the tongue suppressor, enabling the tongue to return to rest in a natural position and engaging the papillae of the tongue.

* * * * *